(12) United States Patent
Dihora et al.

(10) Patent No.: US 11,969,491 B1
(45) Date of Patent: Apr. 30, 2024

(54) pH TRIGGERED RELEASE PARTICLE (71) Applicant: TRUCAPSOL LLC, Bethlehem, PA (US)

(72) Inventors: Jiten Odhavji Dihora, Center Valley, PA (US); Praveen Bachawala, Allentown, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 0 days.

(21) Appl. No.: 18/112,781

(22) Filed: Feb. 22, 2023

(51) Int. Cl.
*A61K 8/14* (2006.01)
*A23L 27/00* (2016.01)
*A23P 10/35* (2016.01)

(52) U.S. Cl.
CPC ............... *A61K 8/14* (2013.01); *A23L 27/72* (2016.08); *A23L 27/77* (2016.08); *A23P 10/35* (2016.08); *A61K 2800/10* (2013.01); *A61K 2800/412* (2013.01); *A61K 2800/651* (2013.01)

(58) Field of Classification Search
CPC ...................................................... A61K 8/14
See application file for complete search history.

(56) References Cited

U.S. PATENT DOCUMENTS

| | | | |
|---|---|---|---|
| 3,345,358 A | 10/1967 | Inklaar | |
| 3,819,838 A | 6/1974 | Smith et al. | |
| 3,870,542 A | 3/1975 | Ida et al. | |
| 4,076,774 A | 2/1978 | Short | |
| 4,626,471 A | 12/1986 | Chao | |
| 5,015,527 A | 5/1991 | Chao | |
| 5,227,446 A | 7/1993 | Denzinger et al. | |
| 5,550,189 A | 8/1996 | Qin et al. | |
| 5,574,179 A | 11/1996 | Wahl et al. | |
| 5,601,760 A | 2/1997 | Rosenberg | |

(Continued)

FOREIGN PATENT DOCUMENTS

| | | |
|---|---|---|
| CA | 1049335 A | 2/1979 |
| CN | 114539887 A | 5/2022 |

(Continued)

OTHER PUBLICATIONS

Adhesives Magazine (2016). SARTOMER: Acrylate Oliogmer. Available at: https://www.adhesivesmag.com/articles/94922-sartomer-acrylate-oligomer.

(Continued)

*Primary Examiner* — Gina C Justice
(74) *Attorney, Agent, or Firm* — Caesar Rivise, PC (57) ABSTRACT

Disclosed are controlled release particles, each controlled release particle of which includes: (a) a core including at least one hydrophobic active material and an emulsifier which is an oil-soluble or oil-dispersible lecithin emulsifier; and (b) a wall at least partially surrounding the core and including an acid insoluble polymer, a colloidal silica, a water insoluble divalent salt, a film forming polymer, and optionally a powder flow aid, wherein the controlled release particle is configured to retain the at least one hydrophobic active material when exposed to an acidic aqueous solution with a pH less than 6, and to release the at least one hydrophobic active material when exposed to a basic aqueous solution with a pH greater than 7. A method for preparing the particles and compositions containing the particles are also disclosed.

16 Claims, 3 Drawing Sheets

(56) References Cited

U.S. PATENT DOCUMENTS

| | | | |
|---|---|---|---|
| 5,837,747 | A | 11/1998 | Soon-Shiong et al. |
| 6,248,909 | B1 | 6/2001 | Akimoto et al. |
| 6,465,016 | B2 | 10/2002 | Parikh et al. |
| 6,572,919 | B2 | 6/2003 | Westland et al. |
| 6,596,073 | B1 | 7/2003 | Nyssen et al. |
| 6,855,335 | B2 | 2/2005 | Seok et al. |
| 7,431,986 | B2 | 10/2008 | Van Lengerich et al. |
| 8,900,495 | B2 | 12/2014 | Pacorel et al. |
| 8,993,041 | B2 | 3/2015 | To et al. |
| 9,205,395 | B2 | 12/2015 | Yan |
| 9,332,774 | B2 | 5/2016 | Nakhasi et al. |
| 9,416,050 | B2 | 8/2016 | Seidl et al. |
| 9,427,719 | B2 | 8/2016 | Viaud-Massuard et al. |
| 9,714,397 | B2 | 7/2017 | Feng et al. |
| 9,937,477 | B2 | 4/2018 | Zhang et al. |
| 9,944,886 | B2 | 4/2018 | Hitchcock et al. |
| 9,993,401 | B2 | 6/2018 | Barnett et al. |
| 10,188,593 | B2 | 1/2019 | Dihora et al. |
| 11,179,302 | B2 | 11/2021 | Dardelle |
| 11,344,502 | B1 | 5/2022 | Dihora et al. |
| 11,465,117 | B2 | 10/2022 | Bachawala et al. |
| 11,484,857 | B2 | 11/2022 | Bachawala et al. |
| 11,542,392 | B1 | 1/2023 | Multari |
| 11,547,978 | B2 | 1/2023 | Bachawala et al. |
| 11,571,674 | B1 | 2/2023 | Dihora et al. |
| 2002/0169233 | A1 | 11/2002 | Schwantes |
| 2004/0017017 | A1 | 1/2004 | Van Lengerich et al. |
| 2004/0033264 | A1 | 2/2004 | Sawhney |
| 2005/0272628 | A1 | 12/2005 | Meli et al. |
| 2005/0276831 | A1 | 12/2005 | Dihora et al. |
| 2008/0085297 | A1 | 4/2008 | Dave et al. |
| 2008/0103265 | A1 | 5/2008 | Schocker et al. |
| 2008/0167188 | A1 | 7/2008 | Fischer et al. |
| 2009/0209661 | A1 | 8/2009 | Somerville Roberts et al. |
| 2010/0011610 | A1 | 1/2010 | Bittorf et al. |
| 2010/0028451 | A1 | 2/2010 | Kaplan et al. |
| 2011/0052680 | A1 | 3/2011 | Hendrickson et al. |
| 2011/0268778 | A1 | 11/2011 | Dihora et al. |
| 2011/0268802 | A1 | 11/2011 | Dihora et al. |
| 2012/0128752 | A1 | 5/2012 | Loo et al. |
| 2013/0004617 | A1 | 1/2013 | Zhang et al. |
| 2013/0022654 | A1 | 1/2013 | Deshmukh et al. |
| 2013/0084379 | A1 | 4/2013 | Gregson et al. |
| 2013/0239429 | A1 | 9/2013 | Vella et al. |
| 2014/0199244 | A1 | 7/2014 | Rijcken et al. |
| 2014/0335032 | A1 | 11/2014 | Panandiker et al. |
| 2015/0079139 | A1* | 3/2015 | Takehana .......... A61Q 5/12 8/406 |
| 2015/0252312 | A1 | 9/2015 | De Villeneuve et al. |
| 2016/0038428 | A1 | 2/2016 | Harel et al. |
| 2016/0128944 | A1 | 5/2016 | Chawrai et al. |
| 2016/0158121 | A1 | 6/2016 | Lei et al. |
| 2016/0166480 | A1 | 6/2016 | Lei et al. |
| 2016/0206561 | A1 | 7/2016 | Kohane et al. |
| 2016/0228338 | A9 | 8/2016 | Dihora et al. |
| 2017/0165627 | A1 | 6/2017 | Duan et al. |
| 2018/0015009 | A1 | 1/2018 | Soubiran et al. |
| 2018/0042825 | A1 | 2/2018 | Lei et al. |
| 2019/0192444 | A1* | 6/2019 | Barzilay .......... A61K 31/522 |
| 2019/0275490 | A1* | 9/2019 | Bachawala .......... B23Q 16/02 |
| 2021/0045409 | A1 | 2/2021 | Witteveen et al. |
| 2022/0133603 | A1 | 5/2022 | Bachawala et al. |
| 2022/0408771 | A1 | 12/2022 | Dihora |
| 2023/0060181 | A1 | 3/2023 | Dihora et al. |

FOREIGN PATENT DOCUMENTS

| | | |
|---|---|---|
| EP | 0076515 A1 | 4/1983 |
| EP | 0361677 B2 | 11/1993 |
| EP | 0815743 A2 | 1/1998 |
| EP | 1371410 A1 | 12/2003 |
| EP | 1797946 A2 | 6/2007 |
| WO | 9901214 A1 | 1/1999 |
| WO | 0105926 A1 | 1/2001 |
| WO | 03013538 A1 | 2/2003 |
| WO | 2004064971 A2 | 8/2004 |
| WO | 2006024411 A2 | 3/2006 |
| WO | 2007135583 A2 | 11/2007 |
| WO | 2008118133 A2 | 10/2008 |
| WO | 2009098226 A1 | 8/2009 |
| WO | 2011041395 A2 | 4/2011 |
| WO | 2015091877 A1 | 6/2015 |
| WO | 2016071151 A1 | 5/2016 |
| WO | 2017023830 A1 | 2/2017 |
| WO | 2020195132 A1 | 10/2020 |

OTHER PUBLICATIONS

Leung et al. (2017). Enteric coating of micron-size drug particles through a Wurster fluid-bed process. Powder Technology, 317, 247-252.

Luo et al. (2014). Zein-based micro-and nano-particles for drug and nutrient delivery: A review. Journal of Applied Polymer Science, 131(16): 40696, 1-12.

Silverajah et al. (2012). Mechanical, thermal and morphological properties of poly (lactic acid)/epoxidized palm plein blend. Molecules, 17(10), 11729-11747.

Tmakova et al. (2015). Plant-derived surfactants as an alternative to synthetic surfactants: surface and antioxidant activities. Chemical Papers, 70(2), 188-196.

Werner et al. (2007). Air-suspension particle coating in the food industry: Part I—State of the art. Powder Technology, 171(1), 25-33.

English language abstract for WO 2009098226 A1 (2009).

English language abstract for WO 2020195132 A1 (2020).

http://polymerdatabase.com/polymer%20physics/sigma.html downloaded on Apr. 29, 2022.

Ko et al., "Characterization of hydrophilic-hydrophobic polymeric surfaces by contact angle measurements", Journal of Colloid and Interface Science, vol. 82(1) (1981).

OECD 301D method (OECD 1992, Test No. 301 Ready Biodegradability, OECD Guidelines for the Testing of Chemicals, Section 3, OECD Publishing, Paris, https://doi.org/10.1787/9789264070349-en.

Thakore et al. (2001). "Studies on biodegradability, morphology and thermo-mechanical properties of LDPE/modified starch blends." European polymer journal, 37(1), 151-160.

Jardine. (2022). Amino-functionalized polysaccharide derivatives: Synthesis, properties and application. Current Research in Green and Sustainable Chemistry 5, 100309.

Gasparini et al. (2020). Quantification of residual perfume by Py-GC-MS in fragrance encapsulate polymeric materials intended for biodegradation tests. Molecules, 25, 718.

Larson et al. (2017). Bulky polar additives that greatly reduce the viscosity of concentrated solutions of therapeutic monoclonal antibodies. Journal of Pharmaceutical Sciences, 106, 1211-1217.

Guo et al. (2012). Structure-activity relationship for hydrophobic salts as viscosity-lowering excipients for concentrated solutions of monoclonal antibodies. Pharm Res, 3102-3109.

Kumar et al. (2017). Viscosity-reducing bulky-salt excipients prevent gelation of protein, but not carbohydrate, solutions. Appl Biochem Biotechnol, 1491-1496.

Wang et al. (2021). Hofmeister effect on the viscosity properties of gelatin in dilute solutions. Colloids and Surfaces B: Biointerfaces, 206, 111944.

* cited by examiner

FIG. 4 pH TRIGGERED RELEASE PARTICLE

BACKGROUND OF THE INVENTION

Field of Invention

This invention relates to controlled release compositions, encapsulation compositions and methods for making and using them.

Description of Related Art

There are many microencapsulated delivery systems disclosed in the art to achieve pH triggered release of actives, especially pharmaceutical actives. However, such delivery systems utilize materials that are not Generally Regarded as Safe (GRAS), such as acrylate copolymers that are coated onto tablets. The process to manufacture and apply such materials onto delivery systems is complex, expensive, and often requires multiple steps.

Many beverage formulations are acidic in nature. Often it is desired to stabilize actives in a microcapsule while suspended in an acidic formulation, and subsequently release the active upon an increase in pH of the formulation, e.g., ingestion of the acidic beverage and release of the active ingredient in the gut. Many household cleaning formulations are acidic in nature. It is difficult to formulate fragrance compositions for such formulations without the acidic conditions hydrolyzing fragrance esters, and changing the scent profile. It is desired to stabilize actives in acidic household cleaning formulations, and subsequently release them over a long duration of time as the pH of the surrounding fluid increases over time (e.g., toilet bowl cleaning formulations, bathroom cleaning products).

EP0076515A1 teaches a controlled release particle that releases active in the intestinal tract but shows retarded release in the stomach. A core material is dispersed in a solution containing ethylcellulose and a wall coating is formed around the particles of the core by temperature induced phase separation of ethylcellulose. EP0076515A1 teach the incorporation of a water soluble ingredient that dissolves in water in an acidic solution having a pH of about 1.2 during the process of phase separation of the ethylcellulose and recovering the particles by centrifugation, filtration, or decantation. Said particle has several deficiencies: 1) the use of toxic organic solvents to solubilize the ethylcellulose, 2) the premature release of the core material when particles are placed in an acidic solution (the described particles would be useful in an anhydrous product, not in a fluid product) and 3) an expensive process to manufacture the particles, isolate the particles, and purify the particles.

EP0361677B2 teaches the use of ethyl acrylate and methacrylic acid copolymers made by emulsion polymerization dissolved in ammonia to prepare particles. The active ingredient is dispersed in the polymer suspension and the ammonia is driven off by azeotropic distillation to yield beads that are then separated and dried. The resultant beads do not swell in the acid conditions of the stomach, but eventually dissolve when moved to an area of higher pH. Such particles require 10:1 to 19:1 ratio of polymer:active, utilize non-GRAS materials, and require an expensive process to manufacture, isolate, and purify the particles.

U.S. Pat. No. 8,993,041B2 teaches dry adhesion of nanometer sized silica particles to a larger size active pharmaceutical ingredient, and then further coating this particle using a fluid bed dryer with a water soluble polymer. The preparation process relies on cohesion of the nanosilica particles to the larger sized active particle remaining intact during the fluidization process, thus such a process can only work when the active pharmaceutical active ingredient and the nanoparticle are compatible or have cohesive strength. Long cycle times are necessary in the fluid bed dryer to achieve a uniform coating of particles. A fluid bed dryer is generally incapable of coating less than 100 micron particles (these lower size particles would be carried away in the fluid bed air stream).

U.S. Pat. No. 9,416,050B2 teaches a crosslinked shellac particle that encapsulates an accelerator for concrete curing in a core/shell capsule using a fluid bed dryer process. The particle is anhydrous and can be blended with the concrete mix to extend the workability time to 8 hours; however, the water swellability of shellac renders the particles to be not useful for acidic formulations. That is, a particle comprising only shellac or crosslinked shellac is not suitable to survive an aqueous environment at low pH.

Hence, there is a need for controlled release particles that do not prematurely release the encapsulated active in a fluid formulation having acidic pH, do not employ toxic solvents during the manufacturing process, utilize GRAS materials, provide particles less than 100 microns in diameter, and utilize a cost effective manufacturing process.

It is desired to develop a delivery system that can stabilize an active in a low pH aqueous formulation using GRAS materials. It is further desired to maintain chemical stability of the active during the manufacturing process and/or during the transport, storage, and distribution of the formulation comprising the delivery system. It is further desired to release the active material upon a change in pH of the surrounding medium.

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

Accordingly, a first aspect of the invention comprises controlled release particles, each controlled release particle of which comprises: (a) a core comprising at least one hydrophobic active material and an emulsifier which is an oil-soluble or oil-dispersible lecithin emulsifier; and (b) a wall at least partially surrounding the core and comprising: an acid insoluble polymer, a colloidal silica, a water insoluble divalent salt, a film forming polymer; and optionally a powder flow aid, wherein the controlled release particle is configured to retain the at least one hydrophobic active material when exposed to an acidic aqueous solution with a pH less than 6, and to release the at least one hydrophobic active material when exposed to a basic aqueous solution with a pH greater than 7.

In certain embodiments, the emulsifier is a member selected from the group consisting of nonionic surfactants and phospholipids.

In certain embodiments, the acid insoluble polymer is a member selected from the group consisting of shellac, alginic acid and fatty acids.

In certain embodiments, the colloidal silica is an aqueous suspension of silica particles with a median particle size from 6 nm to 40 nm.

In certain embodiments, the water insoluble divalent salt is a member selected from the group consisting of calcium carbonate, calcium metasilicate, calcium sulfate, calcium oxalate, dicalcium phosphate and calcium tartrate.

In certain embodiments, the film forming polymer is a member selected from the group consisting of polysaccharides, modified polysaccharides, proteins, celluloses, carboxymethyl cellulose, mannitol and carboxymethyl chitosan.

In certain embodiments, the controlled release particles comprise the powder flow aid, which is a member selected from the group consisting of fumed silica, precipitated silica, calcium silicate, aluminosilicate and combinations thereof.

In certain embodiments, the at least one hydrophobic active material comprises a member selected from the group consisting of a flavorant, an essential oil, a sweetener, an active pharmaceutical ingredient, a vitamin oil, a vegetable oil, a nutraceutical active and a triglyceride.

In some of these embodiments, the at least one hydrophobic active material further comprises a diluent selected from the group consisting of plant waxes, animal waxes, petroleum based waxes, synthetic waxes, mineral waxes, brominated oils, hydrophobically modified inorganic particles, nonionic emulsifiers and oil thickening agents. The diluent is used to change the properties of the hydrophobic material, for example, the polarity, the melting point, the surface tension, the viscosity, the density, or the volatility of the hydrophobic active.

In certain embodiments, the controlled release particles have a diameter from 0.1 microns to less than 100 microns.

A second aspect of the invention comprises a composition comprising the controlled release particles of the invention, wherein the composition is a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, a diaper, a nutraceutical supplement, a skin care product, a baby care product, a family care product, a feminine care product or a household care product.

In certain embodiments, the composition further comprises at least one suspension agent to suspend the controlled release particles in a liquid medium, wherein the at least one suspension agent is at least one member selected from the group consisting of a rheology modifier, a structurant and a thickener.

In certain embodiments of the composition, the at least one suspension agent has a high shear viscosity at, 20 $\sec^{-1}$ shear rate and at 21° C., of from 1 to 7000 cps and a low shear viscosity, at 0.5 $\sec^{-1}$ shear rate at 21° C., of greater than 1000 cps.

In certain embodiments, the composition has a high shear viscosity, at 20 $\sec^{-1}$ and at 21° C., of from 50 to 3000 cps and a low shear viscosity, at 0.5 $\sec^{-1}$ shear rate at 21° C., of greater than 1000 cps.

In certain embodiments of the composition, the at least one suspension agent is selected from the group consisting of pectin, alginate, gum arabic, carrageenan, gellan gum, xanthan gum, guar gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

A third aspect of the invention comprises a method for preparing the controlled release particles of the invention, said method comprising: (a) preparing a first composition by mixing the at least one hydrophobic active material and the emulsifier; (b) preparing a second composition by mixing the colloidal silica and optionally the film forming polymer to form a homogeneous solution; (c) emulsifying the first composition in the second composition with agitation sufficient to achieve a desired particle size of dispersed particles in a dispersed phase of a resulting emulsion; (d) adding the water insoluble divalent salt into the emulsion; (e) adding the aqueous solution of shellac to the emulsion of step (d); (f) assuring that a final pH of the emulsion of step (e) is from 7.2 to 8.5 to provide a spray-ready emulsion; (h) spray drying the spray-ready emulsion to provide a powder comprising the controlled release particles; and optionally (i) adding a silica flow aid to the powder to provide a modified powder.

BRIEF DESCRIPTION OF SEVERAL VIEWS OF THE DRAWINGS

The invention will be described in conjunction with the following drawings, wherein.

DETAILED DESCRIPTION OF PREFERRED EMBODIMENTS OF THE INVENTION

Glossary

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

Statements herein describing a feature as being included in "certain embodiments" of the invention should be understood to mean that the feature may be present in any one embodiment of the invention, all embodiments of the invention, or any combination of two or more embodiments of the invention regardless of whether the "certain embodiments" are introduced in the application before or after such a statement.

It should be understood that the order of steps or order for performing certain actions is immaterial so long as the present teachings remain operable. Moreover, two or more steps or actions can be conducted simultaneously.

As used herein, unless otherwise noted, the terms "capsule", "microcapsule" and "particle" are synonyms, which refer to containers for selectively retaining an active ingredient.

As used herein, unless otherwise noted, the terms "shell," "membrane" and "wall" are synonyms, which refer to barriers at least partially surrounding the core of the particles of the invention.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

Particles

The invention addresses one or more of the prior art deficiencies described above by providing controlled release particles. The particles are particularly well-suited for use in encapsulation of hydrophobic, nonpolar materials.

In one embodiment is provided a population of controlled release particle comprising: (a) a core comprising at least one hydrophobic active material and an emulsifier which is an oil-soluble or oil-dispersible lecithin emulsifier; and (b) a wall at least partially surrounding the core comprising:
1) Acid insoluble polymer;
2) Colloidal silica;
3) A water insoluble divalent salt;
4) A film forming polymer; and
5) Optionally, a powder flow aid,
wherein the controlled release particle retains the active material when exposed to an aqueous solution with a pH less than 6, and such controlled release particles release the active material when exposed to an aqueous solution with a pH greater than 7.

The hydrophobic oil is a member selected from the group consisting of a flavorant, an essential oil, a sweetener, an active pharmaceutical ingredient, a vitamin oil, a vegetable oil, a triglyceride, a nutraceutical active. It is present in the particles in an amount effective to stabilize the vitamin material. The amount can be, e.g., 10 wt. % or 25 wt. % or 40 wt. % or 50 wt. % or 65 wt. %, or any value or subrange of values within the range of 10-65 wt. %.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable essential oils include but are not limited to those obtained from thyme, lemongrass, citrus, anise, clove, aniseed, roses, lavender, citronella, *eucalyptus*, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like Suitable active pharmaceutical ingredients include but are not limited to water insoluble materials that have a melting point below 50° C.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of materials that can alter the surface tension of the active phase in the particle are nonionic emulsifiers such as polysorbate-type nonionic surfactant (e.g. Tween™), alcohol ethoyxlate based surfactants (e.g. Genapol™). Examples of oil thickening agents are waxes mentioned above, modified organopolysiloxanes, silicone gums, hydrogenated castor oil, paraffin oils, polyolefins, and the like. The amount of wax material can be, e.g., 0.9 wt. % or 3 wt. % or 3.9 wt. % or 7.5 wt. % or 9 wt. % or 11 wt. %, or any value or subrange of values within the range of 0.9-11 wt. %.

The oil soluble vitamins include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil. Suitable vegetable oils include but are not limited to oils derived from palm, corn, canola, sunflower, safflower, rapeseed, castor, olive, soybean, coconut and the like in both the unsaturated forms and hydrogenated forms, and mixtures thereof.

Suitable nutraceutical actives include but are not limited to polyunsaturated fatty acids, fish oils, minerals, antioxidants, keto-acids, curcumin, dietary fibers, caffeine, probiotics, prebiotics, and the like.

In certain embodiments, the acid insoluble polymer is a member selected from the group consisting of shellac, alginic acid, and fatty acids. Examples of GRAS fatty acids are palimitic acid, stearic acid, oleic acid, linoleic acid, linolenic acid, eicosapentanoic acid, docosahexaenoic acid, and the like. The amount can be, e.g., 10 wt. % or 15 wt. % or 18 wt. % or 23 wt. % or 28 wt. %, or any value or subrange of values within the range of 10-28 wt. %.

In certain embodiments, the film forming polymer is a member selected from the group consisting of polysaccharides and modified polysaccharides, proteins, celluloses, carboxymethyl cellulose, mannitol, and carboxymethyl chitosan. Said polysaccharide is a member selected from the group consisting of octenyl succinic acid anhydride modified starch, gum arabic, xanthan gum, gellan gum, pectin gum, sodium alginate, konjac gum and carboxyalkyl cellulose. Said protein is a member selected from the group consisting of water soluble proteins and water dispersible proteins. Examples of water soluble proteins include, but are not limited to, gelatin, albumin, insulin, whey protein, enzymes, and mixtures thereof. Examples of water dispersible proteins include, but are not limited to casein, pea protein, mung protein, fava bean protein, keratin, collagen, myosin, fibrin, and mixtures thereof. Said cellulosic polymer is a member selected from the group consisting of naturally derived polymers that have a solubility in water greater than 1 wt. %, with a cellulose backbone including, but not limited to, cellulose esters and cellulose ethers. Cellulose esters include cellulose acetate, cellulose acetate-propionate, cellulose acetate butyrate. Cellulose ethers include ethyl cellulose, methyl cellulose, hydroxymethyl cellulose, hydroxyethyl cellulose, hydroxypropyl cellulose, carboxymethyl cellulose, and their salts. For example, where each R is independently selected from H, $CH_2CH(OH)CH_3$, $CH_3$, $CH_2CO_2H$, $CH_2CH_3$ (Hydroxymethyl, methyl, hydroxypropyl, methyl, etc.). The amount can be, e.g., 6.8 wt. % or 10 wt. % or 12 wt. % or 16 wt. % or 19 wt. %, or any value or subrange of values within the range of 6.8-19 wt. %.

In certain embodiments, the colloidal silica is a member selected from the group consisting of suspension in water comprising silica particles with median particle size from 6 nm or 12 nm to 20 nm or 40 nm. The amount can be, e.g., 10 wt. % or 15 wt. % or 18 wt. % or 23 wt. % or 29 wt. %, or any value or subrange of values within the range of 10-29 wt. %.

In certain embodiments, the water insoluble divalent salt is a member selected from the group consisting of calcium carbonate, calcium metasilicate, calcium sulfate, calcium oxalate, dicalcium phosphate and calcium tartrate. The amount can be, e.g., 3.4 wt. % or 5 wt. % or 6 wt. % or 7.8 wt. % or 9.4 wt. %, or any value or subrange of values within the range of 3.4-9.4 wt. %.

In certain embodiments, the powder flow aid is a member selected from the group consisting of fumed silica, precipitated silica, calcium silicate, aluminosilicate, tapioca maltodextrin, potassium silicate, and combinations thereof. The silica flow aid is preferably a precipitated silica and more preferably a fumed silica. Silicas that have a surface area greater than 60 $m^2/g$ are more preferred. Preferred fumed silicas include AERO SIL 200F, SIPERNAT 22 and SIPERNAT 50, SYLOID 244, ZEOTHIX. Alternatively, the silica flow aid comprises calcium silicate, such as Hubersorb 250 or 600 grades sold by Huber Corporation. Alternatively, the silica flow aid is an aluminosilicate such as the Zeolex grades sold by Huber Corporation. The powder flow aid is present in the particles in an amount effective to minimize or eliminate clumping during spray drying. The amount can be, e.g., from 0.2 wt. % or 0.5 wt. % or 1 wt. % or 2 wt. % or 3 wt. %, or any value or subrange of values within the range of 0.2-3 wt. %.

The oil soluble emulsifier is present in the particles of the invention in an amount effective to maintain a stable emulsion during the particle making process. The amount can be, e.g., 0.4 wt. %, or 1.0 wt. % or 1.6 wt. %, or 2.0 wt. %, or 2.6 wt. %, or any value or subrange of values within the range of 0.4-2.6 wt. %.

The oil soluble emulsifier is preferably a member selected from the group consisting of nonionic surfactants and phospholipids. Nonionic emulsifiers are selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, sorbitan esters and monoglycerides. Phospholipids are preferably selected from lecithins, more preferably fluid, deoiled, or fractionated lecithins. Preferred lecithins have greater than 20% by weight of phosphatidylcholine.

Not to be limited by theory, utilizing lecithin as an emulsifier provides two benefits: 1) achieves small particle size of the active material in an oil-in-water emulsion, said small particle size results in better encapsulation of the active, and 2) causes physical adhesion of the membrane materials around the active material. Choosing selective membrane materials is key to achieving the pH triggered release. Utilizing shellac in the wall material provides a means to achieve pH triggered release. Shellac is comprised of organic acids that have little to no solubility under acidic conditions, but these acids become highly soluble at pH above 7. Utilizing an inorganic material that can bind shellac and other wall materials together is key to achieve chemical stability of the active material in the formulation. A process aid can also be used to reduce the surface porosity of the particle during a spray drying process.

The controlled release particles are preferably spherical but non-spherical shapes are also within the scope of the invention. The particles preferably have a diameter from 0.05-250 microns, or from 0.1 microns to less than 100 microns.

Method of Making the Particles

The particles of the invention are provided by a method comprising: (a) preparing a first composition by mixing the hydrophobic active and lecithin emulsifier; (b) preparing a second composition by mixing the colloidal silica and a film forming polymer to form a homogeneous solution; (c) emulsifying the first composition in the second composition with agitation sufficient to achieve a desired particle size of dispersed particles in a dispersed phase of a resulting emulsion; (d) adding the water insoluble divalent salt in to the emulsion; (e) adding the aqueous solution of shellac; (g) assuring that the final pH of the slurry is between 7.2 to 8.5; (g) spray drying the spray-ready emulsion to provide a powder; and (h) optionally, adding a silica flow aid to the powder to provide a modified powder.

Spray drying of the emulsion is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175 to 195° F. (79-91° C.).

The silica flow aid is added to the dry powder to improve the flowability of the powder. Addition of the silica flow aid minimizes the agglomeration of particles during the curing process.

Not to be limited by theory, the acid insoluble polymer coating or surrounding the active material protects premature release of the active while the particle is sitting in an aqueous acidic solution. The colloidal silica suspension is transparent to the naked eye; however, such suspension contains hard spheres of silica that, when water is removed, result on condensation of the silica particles to form Si—O—Si bonds. The condensed material is no longer soluble in water, even when re-dispersed in water at dilute conditions. Hence, the colloidal silica provides an inorganic layer that prevents the ready diffusion of organic substances. The incorporation of a water insoluble divalent salt provides a way to achieve a tightening of the polymer network. Acidic conditions would lead to dissolution of the divalent salt, releasing a divalent cation that is then able to interact with the film forming material to create a tighter physically crosslinked network of polymers to prevent the diffusion of the encapsulated active material. The combination and selection of materials is absolutely critical to achieve the desired functionality in the final particle. Such materials can be combined while maintaining a low viscosity of the suspension, a low water content to reduce the energy required to dry the particles, and permit the use of an economical spray drying process to manufacture the particles.

Advantages of at least some embodiments of the inventive method include:
a) The method is a one-pot process that achieves water insoluble particles at pH below 6, in an anhydrous form.
b) The materials used are GRAS (generally recognized as safe). The environmental fate of these materials meets biodegradability criteria.
c) The inventive composition and method can be used in a variety of applications, including but not limited to foods, flavors, nutraceuticals, pharmaceuticals, household care, personal care and beauty care.
d) The invention can utilize a commercially available, relatively inexpensive spray drying technique to engineer the particle.
e) The invention yields a water insoluble, anhydrous particle that can encapsulate hydrophobic actives with reduced losses under conditions where the pH of the aqueous formulation is below 6.
f) The invention offers release of the active from the controlled release particle when the pH of the aqueous formulation is increased beyond pH 7.

Compositions Containing the Particles

The invention further comprises compositions comprising the controlled release particles. Such compositions include but are not limited to a powdered food product, a fluid food product, a powdered nutritional supplement, a fluid nutritional supplement, a fluid fabric enhancer, a solid fabric enhancer, a solid antiperspirant, a fluid antiperspirant, a solid deodorant, a fluid deodorant, a diaper, a nutraceutical supplement, a skin care product, a baby care product, a family care product, a feminine care product and a household care product.

The fluid compositions preferably further comprise at least one suspension agent to suspend the controlled release particles, wherein the at least one suspension agent is at least one member selected from the group consisting of a rheology modifier, a structurant and a thickener.

The at least one suspension agent preferably has a high shear viscosity at, 20 sec$^{-1}$ shear rate and at 21° C., of from 1 to 7000 cps and a low shear viscosity, at 0.5 sec$^{-1}$ shear rate and at 21° C., of greater than 1000 cps or 1000-200,000 cps. In certain embodiments, the composition has a high shear viscosity, at 20 sec$^{-1}$ and at 21° C., of from 50 to 3000 cps and a low shear viscosity, at 0.5 sec$^{-1}$ shear rate and at 21° C., of greater than 1000 cps or 1000-200,000 cps.

Preferably, the at least one suspension agent is selected from the group consisting of polyacrylates, polymethacrylates, polycarboxylates, pectin, alginate, gum arabic, carrageenan, gellan gum, xanthan gum, guar gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

In certain embodiments, the composition has at least two controlled release technologies, which release different hydrophobic oil compositions and are selected from the group consisting of neat oils, friction-triggered release microcapsules and water-triggered release microcapsules.

The invention will be illustrated in more detail with reference to the following Examples, but it should be understood that the present invention is not deemed to be limited thereto.

EXAMPLES

Materials and Methods

The following is a representative perfume oil composition used for microcapsule making.

TABLE 1

| Perfume oil composition | | |
|---|---|---|
| Material | wt. % | Functionality |
| CITRONELLYL NITRILE | 1.00% | NITRILE |
| TRIPLAL | 0.25% | ALDEHYDE |
| FLORHYDRAL | 0.10% | ALDEHYDE |
| ALDEHYDE C-10 | 0.10% | ALDEHYDE |

TABLE 1-continued

Perfume oil composition

| Material | wt. % | Functionality |
| --- | --- | --- |
| ALDEHYDE C-12 LAURIC | 0.20% | ALDEHYDE |
| ALLYL CYCLOHEXYL PROPIONATE | 1.00% | ESTER |
| CETALOX | 0.20% | FURAN |
| ANISIC ALDEHYDE | 0.10% | ALDEHYDE |
| CYCLACET | 10.00% | ESTER |
| CYCLAPROP | 5.00% | ESTER |
| DIHYDROMYRCENOL | 10.00% | ALCOHOL |
| DIPHENYL OXIDE | 1.00% | OXIDE |
| HABANOLIDE | 2.50% | KETONE |
| YARA YARA | 2.00% | ETHER |
| CIS-3-HEXENYL SALICYLATE | 2.00% | ESTER |
| VERDOX | 2.50% | ESTER |
| HEXYLCINNAMIC ALDEHYDE | 20.00% | ALDEHYDE |
| BHT | 0.50% | Antioxidant |
| ISO E SUPER | 2.50% | KETONE |
| KOAVONE | 2.50% | KETONE |
| EUCALYPTOL | 0.20% | ALCOHOL |
| MANZANATE, 10% IPM | 0.50% | ESTER |
| MUSCENONE, 10% IPM | 0.50% | KETONE |
| LAEVO CARVONE, 10% IPM | 0.50% | KETONE |
| METHYL ANTHRANILATE | 0.10% | ESTER |
| METHYL IONONE GAMMA | 1.25% | KETONE |
| LILIAL | 10.00% | ALDEHYDE |
| ALDEHYDE C-12 MNA, 10% DPG | 0.50% | ALDEHYDE |
| MYRAC ALDEHYDE | 0.50% | ALDEHYDE |
| D-LIMONENE | 5.00% | TERPENE |
| PEONILE | 2.50% | NITRILE |
| ETHYLENE BRASSYLATE | 12.50% | ESTER |
| PHENOXANOL | 2.50% | ALCOHOL |

Thermal Gravimetric Analysis

A Thermal Gravimetric Analysis pan is exposed to a Bunsen burner to remove any residue from the pan. Approximately 5 milligrams of sample is weighed onto a pan of a Thermal Gravimetric Analyzer (Model TGA Q500). Next the sample is exposed to a temperature ramp that comprises from an initial temperature of 25° C., a heating ramp of 10° C. per minute, to a final temperature of 600° C. A graph of sample mass loss versus temperature is plotted to gain insights into transitions—water evaporation, volatile active evaporation, degradation of the microcapsule materials.

Differential Scanning Calorimetry

Approximately 5 milligrams of sample is weighed onto a pan of a Differential Scanning calorimeter (Model DSC Q2000) and hermetically sealed. The sample pan is then exposed to a temperature ramp that comprises from an initial temperature of 25° C., a heating ramp of 10° C. per minute, to a final temperature of 250° C., and then a temperature decrease ramp of negative 10° C. per minute, to a final temperature of 25° C. A graph of heat flow versus temperature provides insights into thermal transitions that occur in the powder.

Free Oil

Approximately 0.100 grams of spray dried powder is added to 1% Citric Acid solution in water in a 40 mL scintillation vial and agitated for 30 minutes. Approximately 10 mL of hexane is added and the scintillation vial is overturned 10 times to allow for mixing. The scintillation vial is then placed on a platform shaker that shakes the vial at a frequency of 1/sec to allow for mixing of the contents, for 10 minutes. The scintillation vial is allowed to sit unagitated at room temperature for 10 minutes. Sodium sulfate or sodium chloride could be added if there is a lack of phase separation of the hexane layer observed. Approximately 3 mL of the clear hexane layer is removed, placed into a syringe filter (0.45 micron, 25 mm diameter Acrodisc PTFE filter), and decanted into a GC vial. The sample is analyzed by Gas Chromatography. GC conditions are shown in Table 3 below.

TABLE 2

GC CONDITIONS

Oven

Initial Temperature: 40° C.
Rate: 5° C./min to 250° C.
Hold Time at Inlet Temp: 2 minutes
Run Time: 44.00 minutes
Inlet Mode: Split
Split Ratio: 8:1
Initial Temperature: 240° C.
Column Flow: 1.2mL/min (constant flow mode)
Column Type: DB-5, 30 m, 0.25 mm duameter,
0.25 μm film thickness
Basic MSD Settings Low Mass: 50
High Mass: 550
Threshold: 500
MS Quad Temperature: 150° C.
MS Source Temperature: 230° C.
Transfer Line Temperature: 250° C.

The quantity of oil extracted is calculated by summing the area counts of all of the peaks and referencing a standard calibration curve to translate the area counts to milligrams of perfume per milliliter of hexane (such standard curve was developed by preparing various amounts of fragrance oil in 1% citric acid solution, that is then extracted using hexane). The calculated free oil % is the milligrams of perfume extracted in the sample/milligrams of perfume theoretically in the sample (0.100 grams×50 wt. % oil in particle=0.050 grams or 50 milligrams)×100%.

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle morphology.

Example 1: TCJD013123-D [No Colloidal Silica]

Approximately 3.0 g of sunflower lecithin is mixed with 75 g of fragrance oil for 30 minutes at room temperature to obtain a homogenous solution. The oil mixture is emulsified in 420 g of 10 wt. % Peptiplus XP solution using an Ultra Turrax T25 mixer for 4 minutes at 18,000 RPM. Next 7.5 g of fine calcium carbonate powder is dispersed in the mixture. Then, approximately 86 g of 26 wt. % shellac solution is added to form a final mixture. The mixture is spray dried using a co-current 3 ft (91.4 cm) diameter Niro spray dryer using a two-fluid nozzle with air pressure of 65 psig, an inlet air temperature of 395° F. (202° C.), an outlet air temperature of 188° F. (86.7° C.), and a flowrate of 50 mL/min to yield 13-20 micron particles.

Example 2—TCJD012723-C [No Divalent Salt]

Approximately 3.0 g of sunflower lecithin is mixed with 75 grams of fragrance oil for 30 minutes at room temperature to obtain a homogenous solution. The oil mixture is emulsified in a solution consisting of 91 g of 40 wt. % colloidal silica solution diluted with 90 g of water using an Ultra Turrax T25 mixer for 4 minutes at 18,000 RPM. Then, approximately 139 g of 26 wt. % shellac solution is added to form a final mixture. The mixture is spray dried using a co-curent 3 ft (91.4 cm) diameter Niro spray dryer using a two-fluid nozzle with air pressure of 65 psig, an inlet air temperature of 395° F. (202° C.), an outlet air temperature of 188° F. (86.7° C.), and a flowrate of 50 mL/min to yield 13-20 micron particles.

Examples 3A—TCJD013123-A [Film Former]

Approximately 3.0 g of sunflower lecithin is mixed with 75 grams of fragrance oil for 30 minutes at room temperature to obtain a homogenous solution. The oil mixture is emulsified in a solution consisting of 57 g of 40 wt. % colloidal silica solution mixed with 180 g of 10 wt. % Peptiplus XP solution diluted with 36.5 g of water using an Ultra Turrax T25 mixer for 4 minutes at 18,000 RPM. Next, approximately 7.5 g of fine calcium carbonate powder is dispersed in the mixture. Then, approximately 88 g of 26 wt. % shellac solution is added to form a final mixture. The mixture is spray dried using a co-curent 3 ft (91.4 cm) diameter Niro spray dryer using a two-fluid nozzle with air pressure of 65 psig, an inlet air temperature of 395° F. (202° C.), an outlet air temperature of 188° F. (86.7° C.), and a flowrate of 50 mL/min to yield 13-20 micron particles.

Example 3B—TCJD013123-E [Film Formers]

Approximately 3.0 g of sunflower lecithin is mixed with 75 grams of fragrance oil for 30 minutes at room temperature to obtain a homogenous solution. The oil mixture is emulsified in a solution consisting of 57 g of 40 wt. % colloidal silica solution mixed with 105 g of 10 wt. % Peptiplus XP solution mixed with 500 g of a 1.5 wt. % solution of sodium alginate using an Ultra Turrax T25 mixer for 4 minutes at 18,000 RPM. Next, approximately 7.5 grams of fine calcium carbonate powder is dispersed in the mixture. Then, approximately 88 g of 26 wt. % shellac solution is added to form a final mixture. The mixture is spray dried using a co-current 3 ft (91.4 cm) diameter Niro spray dryer using a two-fluid nozzle with air pressure of 65 psig, an inlet air temperature of 395° F. (202° C.), an outlet air temperature of 188° F. (86.7° C.), and a flowrate of 50 mL/min to yield 13-20 micron particles

Example-3C—TCJD013123-B [Higher Shellac]

Approximately 3.0 g of sunflower lecithin is mixed with 75 grams of fragrance oil for 30 minutes at room temperature to obtain a homogenous solution. The oil mixture is emulsified in a solution consisting of 57 g of 40 wt. % colloidal silica solution mixed with 180 g of 10 wt. % Peptiplus XP solution diluted with 36.5 g of water using an Ultra Turrax T25 mixer for 4 minutes at 18,000 RPM. Next, approximately 9.9 g of fine calcium carbonate powder is dispersed in the mixture. Then, approximately 116 g of 26 wt. % shellac solution is added to form a final mixture. The mixture is spray dried using a co-curent 3 ft (91.4 cm) diameter Niro spray dryer using a two-fluid nozzle with air pressure of 65 psig, an inlet air temperature of 395° F. (202° C.), an outlet air temperature of 188° F. (86.7° C.), and a flowrate of 50 mL/min to yield 13-20 micron particles.

Example 3D—Flavor Particles

Particles identical to Example 3B are prepared, but the fragrance oil is replaced with a representative flavor oil composition.

Example 4. Stability Testing of Various Powders

Powders of Examples 1 to 3 were evaluated for Free Oil to understand the leakage of the encapsulated fragrance oil in an acidic formulation. The results are provided below.

TABLE 3

| Example | % Free Oil |
|---|---|
| 1 | 21.8% |
| 2 | 7.1% |
| 3A | 13.9% |
| 3B | 0.79% |
| 3C | 13.4% |

It is apparent from the free oil data above that the absence of colloidal silica in the particle leads to large leakage of the encapsulated fragrance oil (Example 1). Even in the absence of divalent salt, the acid insoluble polymer is able to retain the encapsulated active (Example 2). The quantity of acid insoluble polymer in the particle really does not produce a significant effect on free oil (Examples 3A and 3C). The combination of colloidal silica, divalent salt, acid insoluble polymer, a combination of film forming materials produces a particle that can protect the encapsulated active material extremely well (Example 3B).

Figure 1:
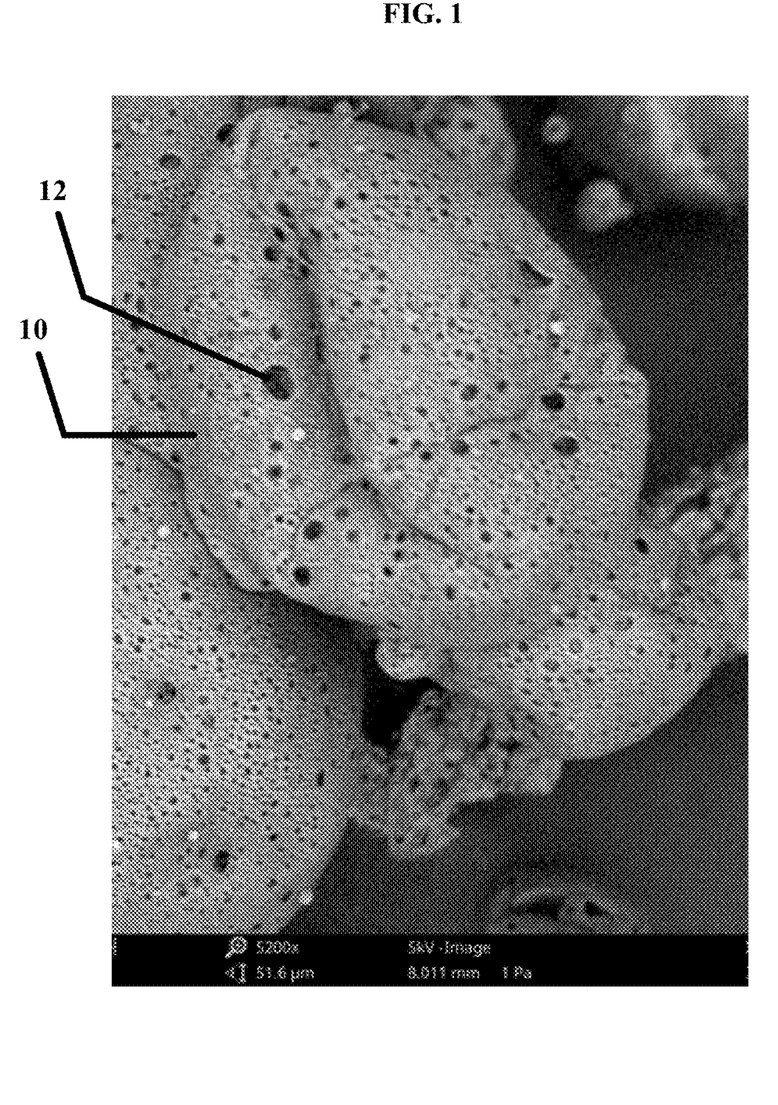
FIG. 1 is a Scanning Electron Microscopy image of the spray dried powder of Example 3B, including pores 12 on the surface of spray dried particle 10.
Figure 2:
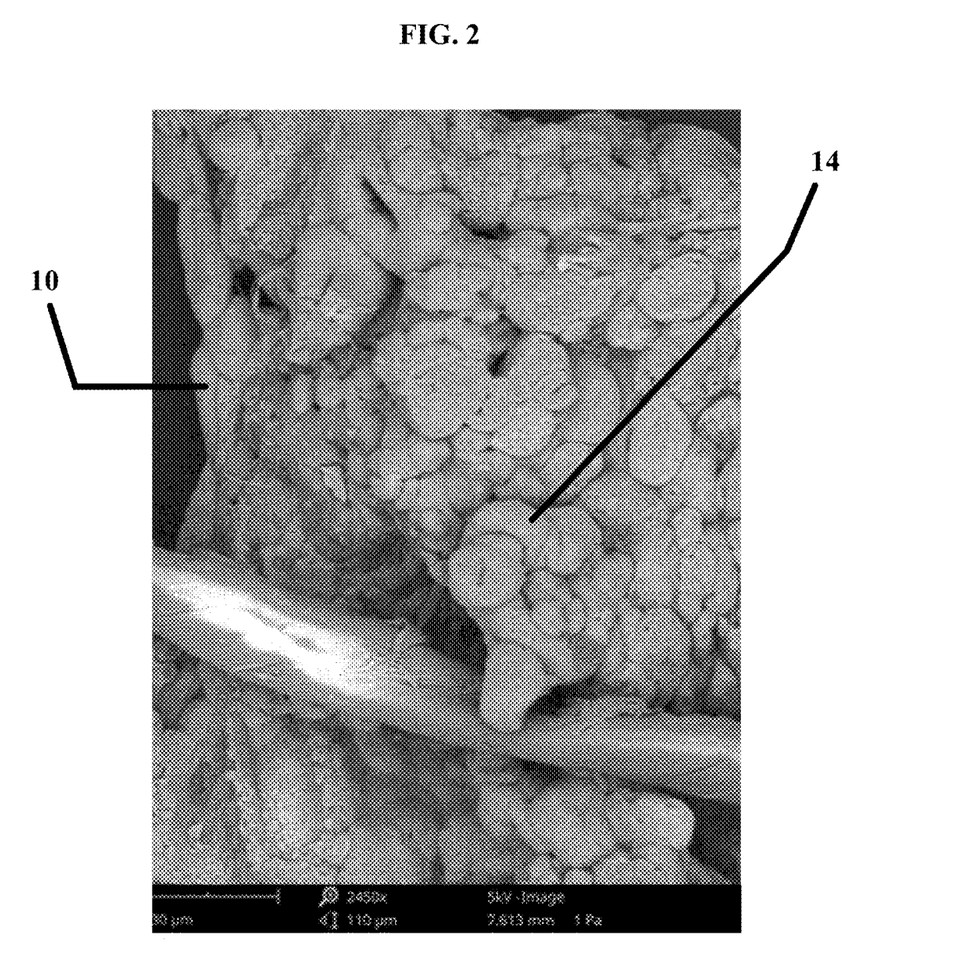
FIG. 2 is a Scanning Electron Microscopy image of Example 3B powder in 1% citric acid solution (pH 3), including sealed pores 14 of spray dried particle 10.
Figure 3:
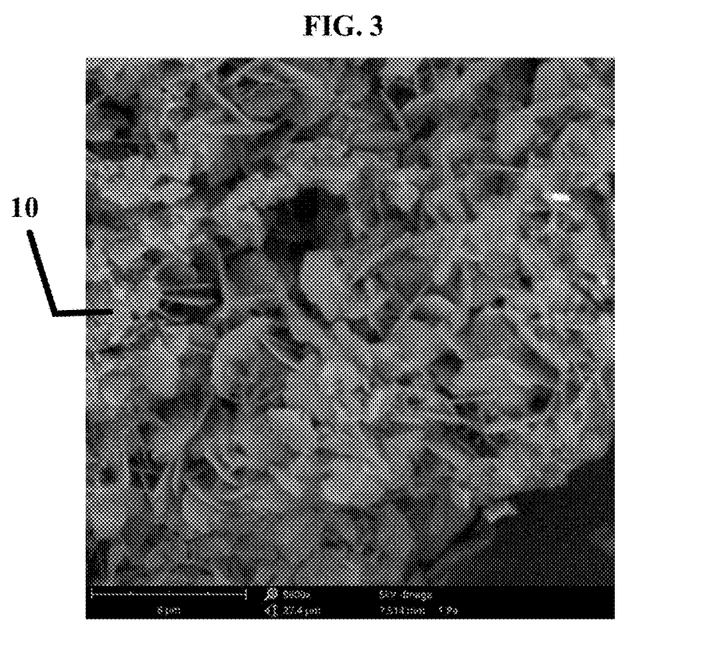
FIG. 3 is a Scanning Electron Microscopy image of Example 3B powder initially in pH 3 water, whose pH is adjusted to in pH 7 using 10% sodium hydroxide solution, including particles 10 having increased porosity.
Figure 4:
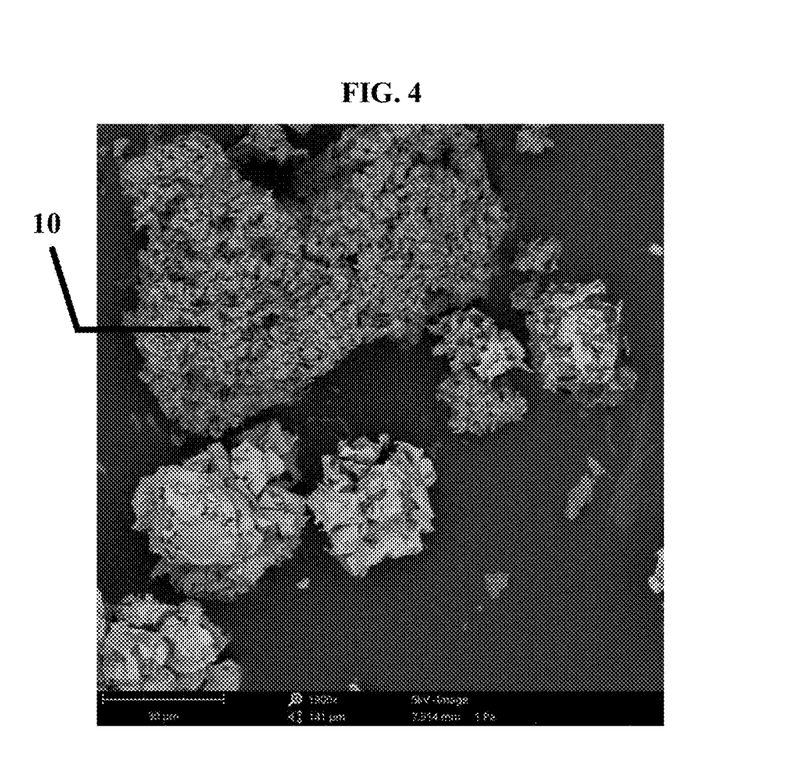
FIG. 4 is a lower magnification view of the Example 3B powder shown in FIG. 3.

When these particles are removed from the pH 3 solution of citric acid, and placed in a pH 7.2 solution in water, a disintegration of the particle is observed, and release of the encapsulated active happens, as shown in FIG. 3

Example 5. Acidic Household Cleaning Formulation

Table 4. Acidic Household Cleaning Formulation examples

The following is a representative list of acidic cleaning formulations into which applicant's microcapsules can be formulated. Such microcapsules retain the fragrance oil while in the acidic formulation, but start to release the fragrance oil when the pH of the surrounding medium is adjusted higher.

| Ingredient | 4A | 4B | 4C |
|---|---|---|---|
| Lactic Acid | 4.00% | 0.00% | 5.00% |
| Citric Acid | 0.00% | 13.71% | 0.00% |
| Sodium Dodecylbenzene Sulfonate | 1.56% | 0.00% | 0.00% |
| Alkyl Polyglucoside (APG-215) | 0.63% | 2.96% | 0.00% |
| Sodium Lauryl Sulfate | 0.00% | 0.00% | 1.00% |
| C12-C14 Fatty Alcohol | 0.00% | 0.00% | 1.60% |
| Sodium Hydroxide | 0.18% | 0.00% | 0.50% |
| Example 3B Fragrance particles | 1.00% | 1.00% | 1.00% |
| Neat Fragrance oil | 0.10% | 0.10% | 0.10% |
| Water | 92.53% | 82.23% | 90.80% |

Example 6. Acidic Beverage Formulation

The following is a representative acidic beverage formulation into which applicant's microcapsules can be formulated. Such microcapsules retain the flavor oil while in the acidic formulation, but start to release the flavor when the pH of the surrounding medium is adjusted higher.

TABLE 5

Acidic Beverage Formulation

| Ingredient | wt. % |
| --- | --- |
| Water | 84.09% |
| High Fructose Corn Syrup | 14.10% |
| Malic Acid | 0.45% |
| Citric Acid | 0.61% |
| Sodium Cirate | 0.11% |
| Tricalcium Phosphate | 0.02% |
| Potassium Sorbate | 0.08% |
| Ascorbic Acid | 0.04% |
| Example 3D particles with flavor oil | 0.50% |
| | 100.00% |

A beverage having the above composition is prepared as follows: Water and high fructose corn syrup (HFCS) are blended together. Citric and malic acids are added to the water and sugar mixture until dissolved. Sodium citrate, tricalcium phosphate, and potassium sorbate are then added and dissolved. Finally ascorbic acid and Example 3D particles are added under high agitation to assure homogeneous distribution and no aggregation of particles.

While the invention has been described in detail and with reference to specific examples thereof, it will be apparent to one skilled in the art that various changes and modifications can be made therein without departing from the spirit and scope thereof.

What is claimed is:

1. Controlled release particles, each controlled release particle of which comprises:
   a core comprising at least one hydrophobic active material and an emulsifier which is an oil-soluble or oil-dispersible lecithin emulsifier; and
   a wall at least partially surrounding the core and comprising:
   an acid insoluble polymer;
   a colloidal silica;
   a water insoluble divalent salt;
   a film forming polymer; and optionally
   a powder flow aid,
   wherein: (a) the controlled release particle is configured to retain the at least one hydrophobic active material when exposed to an acidic aqueous solution with a pH less than 6, and to release the at least one hydrophobic active material when exposed to a basic aqueous solution with a pH greater than 7, (b) the acid insoluble polymer and the film forming polymer are water soluble, and (c) the formation of the wall does not require the use of organic solvents in the core or wall.

2. The controlled release particles of claim 1, wherein the emulsifier is a member selected from the group consisting of nonionic surfactants and phospholipids.

3. The controlled release particles of claim 1, wherein the acid insoluble polymer is a member selected from the group consisting of shellac and alginic acid.

4. The controlled release particles of claim 1, wherein the colloidal silica is an aqueous suspension of silica particles with a median particle size from 6 nm to 40 nm.

5. The controlled release particles of claim 1, wherein the water insoluble divalent salt is a member selected from the group consisting of calcium carbonate, calcium metasilicate, calcium sulfate, calcium oxalate, dicalcium phosphate and calcium tartrate.

6. The controlled release particles of claim 1, wherein the film forming polymer is a member selected from the group consisting of polysaccharides, modified polysaccharides, proteins, celluloses, carboxymethyl cellulose, mannitol and carboxymethyl chitosan.

7. The controlled release particles of claim 1, comprising the powder flow aid which is a member selected from the group consisting of fumed silica, precipitated silica, calcium silicate, aluminosilicate and combinations thereof.

8. The controlled release particles of claim 1, wherein the at least one hydrophobic active material comprises a member selected from the group consisting of a flavorant, an essential oil, a sweetener, an active pharmaceutical ingredient, a vitamin oil, a vegetable oil, a nutraceutical active and a triglyceride.

9. The controlled release particles of claim 8, wherein the at least one hydrophobic active material further comprises a diluent selected from the group consisting of plant waxes, animal waxes, petroleum based waxes, synthetic waxes, mineral waxes, brominated oils, hydrophobically modified inorganic particles, nonionic emulsifiers and oil thickening agents.

10. The controlled release particles of claim 1, which have a diameter from 0.1 microns to less than 100 microns.

11. A composition comprising the controlled release particles of claim 1, wherein the composition is a powdered food product, a fluid food product, a powdered nutritional supplement, a fluid nutritional supplement, a fluid fabric enhancer, a solid fabric enhancer, a fluid shampoo, a solid shampoo, hair conditioner, body wash, solid antiperspirant, fluid antiperspirant, solid deodorant, fluid deodorant, fluid detergent, solid detergent, a diaper, a nutraceutical supplement, a skin care product, a baby care product, a family care product, a feminine care product or a household care product.

12. The composition of claim 11, further comprising at least one suspension agent to suspend the controlled release particles in a liquid medium, wherein the at least one suspension agent is at least one member selected from the group consisting of a rheology modifier, a structurant and a thickener.

13. The composition of claim 12, wherein the at least one suspension agent has a high shear viscosity, at 20 $sec^{-1}$ shear rate and at 21° C., of from 1 to 7000 cps and a low shear viscosity, at 0.5 $sec^{-1}$ shear rate at 21° C., of greater than 1000 cps.

14. The composition of claim 12, which has a high shear viscosity, at 20 $sec^{-1}$ and at 21° C., of from 50 to 3000 cps and a low shear viscosity, at 0.5 $sec^{-1}$ shear rate at 21° C., of greater than 1000 cps.

15. The composition of claim 12, wherein the at least one suspension agent is selected from the group consisting of pectin, alginate, gum arabic, carrageenan, gellan gum, xanthan gum, guar gum, hydroxyl-containing fatty acids, hydroxyl-containing fatty esters, hydroxyl-containing fatty waxes, castor oil, castor oil derivatives, hydrogenated castor oil derivatives, hydrogenated castor wax and mixtures thereof.

16. A method for preparing the controlled release particles of claim 1, said method comprising:
   (a) preparing a first composition by mixing the at least one hydrophobic active material and the emulsifier;

(b) preparing a second composition by mixing the colloidal silica and optionally the film forming polymer to form a homogeneous solution;
(c) emulsifying the first composition in the second composition with agitation sufficient to achieve a desired particle size of dispersed particles in a dispersed phase of a resulting emulsion;
(d) adding the water insoluble divalent salt into the emulsion;
(e) adding the aqueous solution of shellac to the emulsion of step (d);
(f) assuring that a final pH of the emulsion of step (e) is from 7.2 to 8.5 to provide a spray-ready emulsion;

(h) spray drying the spray-ready emulsion to provide a powder comprising the controlled release particles; and optionally (i) adding a silica flow aid to the powder to provide a modified powder.

* * * * *